United States Patent
Enari et al.

(10) Patent No.: US 8,124,131 B2
(45) Date of Patent: Feb. 28, 2012

(54) FOOD INTAKE REGULATOR

(75) Inventors: Hiroyuki Enari, Ibaraki (JP); Masataka Kawarasaki, Ibaraki (JP)

(73) Assignee: Maruha Nichiro Foods, Inc. (JP)

( * ) Notice: Subject to any disclaimer, the term of this patent is extended or adjusted under 35 U.S.C. 154(b) by 232 days.

(21) Appl. No.: 12/398,006

(22) Filed: Mar. 4, 2009

(65) Prior Publication Data

US 2009/0226535 A1 Sep. 10, 2009

(30) Foreign Application Priority Data

Mar. 4, 2008 (JP) ................................. 2008-054091

(51) Int. Cl.
*A61K 35/55* (2006.01)
(52) U.S. Cl. ....................................... 424/565; 424/570
(58) Field of Classification Search ........................ None
See application file for complete search history.

(56) References Cited

U.S. PATENT DOCUMENTS

2009/0275500 A1* 11/2009 Enari et al. ...................... 514/11

FOREIGN PATENT DOCUMENTS

| CN | 1141740 A | 2/1997 |
|---|---|---|
| CN | 1480158 A | 3/2004 |
| JP | 61-239847 A | 10/1986 |
| JP | 4-141050 A | 5/1992 |
| JP | 9-20675 A | 1/1997 |
| JP | 2000-515139 A | 11/2000 |
| JP | 2002-53474 A | 2/2002 |
| JP | 2002-284683 A | 10/2002 |
| JP | 2005-82490 A | 3/2005 |
| WO | 2005/049833 A1 | 6/2005 |
| WO | 2006/137597 A1 | 12/2006 |

OTHER PUBLICATIONS

Tritos et al., Diabetes, 1998, vol. 47, p. 1687-1692.*
Shimada et al.; "Mice lacking melanin-concentrating hormone are hypophagic and lean"; Nature; vol. 396; Dec. 17, 1998; , pp. 670-673.
Rossi et al.; "Melanin-Concentrating Hormone Acutely Stimulates Feeding, But Chronic Administration Has No Effect on Body Weight"; Endocrinology; vol. 138 (No. 1) 1997 pp. 351-355.
EPO Examination Report for Application No. 09 154 302.5-2107 mailed on Jun. 10, 2011.
Plisetskaya, E.M. et al., "Does Salmon Brain Produce Insulin?", Gen Comp Endocrinol.,1993;91:74-80.
Amano, M. et al., Immunocytochemical localization and ontogenic development of alpha-melanocyte-stimulating hormone (alpha-MSH) in the brain of a pleuronectiform fish, barfin flounder, Cell Tissue Res, 2005, vol. 320, No. 1, p. 127-134.
Maruyama, K. et al., Isolation and Characterization of Neuromedin U From the Goldfish, Proc. Jpn. Soc. Comp. Endocrinol, 2006, No. 21, p. 76.
Wada, K. et. al., Effect of Octadecaneuropeptide on Food Intake and Locomotor Activity in the Goldfish, *Carassius auratus*, Proc. Jpn. Soc. Comp. Endocrinol, 2006, No. 21, p. 79.
Rejection Notice for Japanese Application No. 2008-054091 with English translation dated Jun. 3, 2010.
Okuda H: "Effect of Chondroitin Sulfate Isolated From Salmon Head Cartilage on High Fat Diet-Induced Obesity" Fureguransu Janaru—Fragrance Journal, Fureguransu Janarusha, Tokyo, JP, Jan. 1, 1999, pp. 85-88, XP009007045 ISSN: 0288-9803.
Database WPI Week 200054 Thomson Scientific, London, GB; p. 4, AN 2000-572599 XP 002529274 "Roe powder serial health-care food".
Della-Zuana O et al: "Acute and chronic administration of melanin-concentrating hormone enhances food intake and body weight in Wistar and Sprague-Dawley rats" International Journal of Obesity, vol. 26, No. 10, Oct. 2002, pp. 1289-1295, XP009117401 ISSN: 0307-0565 p. 1295, left-hand column, line 19-line 24.
Masako Shimada et al: "Mice lacking melanin-concentrating hormone are hypophagic and lean" Dec. 17, 1998, Nature Publishing Group, London, UK, pp. 670-674, XP002308086 ISSN: 0028-0836.
Matsuda K et al: "Central administration of melanin-concentrating hormone (MCH) suppresses food intake, but not locomotor activity, in the goldfish, *Carassius auratus*" Neuroscience Letters, Limerick, IE, vol. 399, No. 3, May 22, 2006, pp. 259-263, XP025024251 ISSN: 0304-3940 [retrieved on May 22, 2006].
Hainault I et al: "Anti-Obesity Effect of Dietary Fish Oil: Studies in High Fat Diet and in Genetically Induced Obesities" International Journal of Obesity, Newman Publishing, London, GB, vol. Suppl. 02, No. 18, Jan. 1, 1994, p. 137, XP001073525 ISSN: 0307-0565.
Yada Takashi et al: "Relationships between obesity and metabolic hormones in the "cobalt" variant of rainbow trout" General and Comparative Endocrinology, vol. 128, No. 1, Aug. 2002, pp. 36-43, XP009117391 ISSN:0016-6480.
Database WPI Week 200438 Thomson Scientific, London, GB; AN 2004-401162 XP002529275.
European Search Report for European Application No. 09154302.5-2107 dated Jul. 8, 2009.

* cited by examiner

*Primary Examiner* — Kade Ariani
(74) *Attorney, Agent, or Firm* — Cantor Colburn LLP

(57) ABSTRACT

A safe and widely-applicable food intake regulator can be provided by using at least one of a fish brain and parts thereof, which have the activity to regulate suppress food intake.

9 Claims, 1 Drawing Sheet

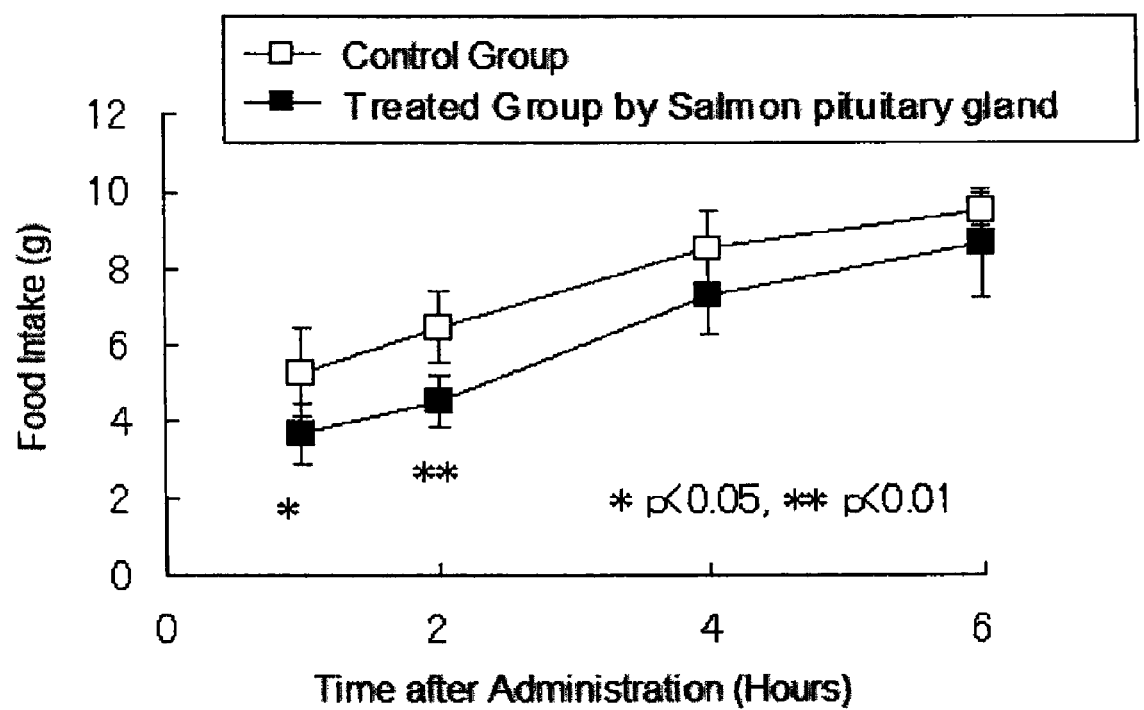

FOOD INTAKE REGULATOR

BACKGROUND OF THE INVENTION

1. Field of the Invention

The present invention relates to a food intake regulator, which contains a fish brain as an active ingredient. The food intake regulator according to the invention is useful in treatment of a disease and improvement of the symptom of the disease that are due to overeating or that require feeding regulation. Therefore, the food intake regulator according to the invention can be widely applied to various foods and pharmaceuticals.

2. Description of the Related Art

About more than half of men and women in their 40s or higher are patients or potential patients of lifestyle-related diseases such as hypertension, diabetes mellitus, and hyperlipidemia. Since most of these diseases are due to obesity, it is desired that obesity be prevented or improved. The best approach to preventing obesity is considered to setting of a regular eating pattern, but it is often difficult to establish and maintain the pattern in the modern age as a time of plenty.

As a substance which regulates, especially suppresses food intake, mazindol as amphetamines is commercially available as a pharmaceutical.

However, the use of mazindol is limited only to patients having severe obesity because of the direct effects of mazindol on the central nervous system and risks of habituation or addiction. Safer approaches for the food intake suppression have been required.

As a method of suppressing food intake, Japanese Patent Laid-Open No. 2000-515139 discloses one using precursors of serotonin, dopamine, norepinephrine and histamine; Japanese Patent Laid-Open No. 1997-20675 discloses one using a fruit body of pleurotus ostreatus; and Japanese Patent Laid-Open No. 2002-53474 discloses one using avocado.

Melanin-concentrating hormone (MCH), which was identified as a substance adaptively controlling pigment aggregation in the pituitary gland of salmon, was also found in the hypothalamus of the mammalian brain and attracts attention as a hormone involved in feeding. Significant body weight loss was found in MCH gene knockout mice with decreased food intake and increased metabolism (Shimada. M, et al., Nature, 396, 670-674, 1998). In addition, after MCH was injected intracerebroventricularly to rats, it was found to stimulate food intake (M. Rossi, et. al., Endocrinology, 138, 351-355, 1997).

SUMMARY OF THE INVENTION

Although MCH is known as a substance involved in food intake, in particular stimulation of food intake as noted above, no reports there is no reports looking at another aspect of MCH as a food intake regulator.

In light of the related art, an object of the present invention is to provide a safe food intake regulator having no side-effects, which can be easily taken though daily diet.

The present inventors have conducted extensive studies to achieve the above object and have reached a new finding that a food intake regulator can be obtained surprisingly by using as an active ingredient the fish brain with a long history of its availability as foods, which has been recognized to be safe by experience. For example, the brain part of a salmon has a weight of several decades to several thousand milligrams, while the head part of a salmon has a weight of about 300 g to 400 g. A highly concentrated fish brain expresses the food intake suppression activity. These findings have led the inventors to complete the invention.

Therefore, a food intake regulator according to the present invention is characterized in comprising one or more active ingredients selected from the group consisting of at least a part of a fish brain and a fish pituitary gland. The present invention further includes the use of at least one of at least a part of a fish brain and a fish pituitary gland for production of food intake regulators, foods, pharmaceuticals and quasi drugs. The present invention relates to a method of treating and/or preventing a disease such as obesity by administrating at least one of at least a part of a fish brain and a fish pituitary gland to a subject necessary to be treated.

The food intake regulator preferably contains an effective amount of the active ingredient to regulate appetite and food intake in mammals. In addition, the food intake regulator can further contain a pharmaceutically acceptable carriers or a dilution. Moreover, the food intake regulators can be provided in the forms as foods, pharmaceuticals and quasi drugs.

According to the present invention, a safe food intake regulator having no side-effects can be supplied, which can be easily taken through daily diet.

BRIEF DESCRIPTION OF THE DRAWING

FIG. 1 is a graph showing the food intakes.

DETAILED DESCRIPTION OF THE PREFERRED EMBODIMENTS

According to the present invention, a fish brain is used as an active ingredient of a food intake regulator. As the fish brain, a fresh brain extracted from a fish head can be used. A lyophilized product can be obtained by rapidly freezing a fresh fish brain in liquid nitrogen and drying the frozen fish brain under a reduced pressure. The lyophilized product can be preferably used according to the desired formulation. As the active ingredient, at least one component can be used, which is selected from the group consisting of the entire brain, parts of the entire brain and a pituitary gland. The parts of the entire brain includes a cerebellum, a lobus olfactorius, an optic stalk, a medulla oblongata, a pituitary gland, a pineal body, a hypothalamus, and parts such as nerves and blood vessels, which contact with the these brain parts. Examples of the fish include salmon, a king salmon and rainbow trout.

The food intake regulator according to the present invention has a food intake suppressing effect. Therefore, the appetite of the target people or the target animals can be regulated by allowing them to take the food intake regulator according to the invention. Since the food intake regulator according to the present invention has anti-obesity effect, the food intake regulator according to the present invention is effective for treatment of patients having obesity or prevention of obesity of potential patients. The food intake regulator according to the present invention is also effective for treatment of disease or improvement of symptoms, which can be achieved by regulation of appetite.

The food intake regulator according to the present invention can be provided as pharmaceutical compositions, foods such as solid food, semi-solid food, and liquid food including beverages and in various other forms. For example, the food intake regulator according to the invention can be provided in various forms such as liquid, emulsion, dispersion, powder, granule, tablet, capsule, paste, and cream.

A agent for treating and/or preventing obesity as one embodiment of the present invention can be produced with at least one of the fish brain and any parts thereof as an active ingredient. In this case, the food intake regulator can be formulated into preparations in forms such as injection, oral solution, tablet, granule, powder, capsule, suppository, ointment, nasal drop, eye drop, and patch, by appropriately mixing the active ingredient with an additive such as an excipient for preparing the food intake regulator, as needed.

Examples of the additives used in the above preparations include magnesium stearate, talc, lactose, dextrin, starches, methyl cellulose, fatty acid glycerides, water, propylene glycol, macrogols, alcohol, crystalline cellulose, hydroxypropyl cellulose, low substituted hydroxypropyl cellulose, carmelloses, povidone, polyvinyl alcohol, and calcium stearate. These additives can be used alone or in combination of two or more of them. In these cases, one or more components selected from colorants, stabilizers, antioxidants, preservatives, pH regulators, tonicity agents, solubilizers and soothing agents can be added as needed. Granules, tablets, and capsules can also be coated with a coating base such as hydroxypropylmethyl cellulose or hydroxypropylmethyl cellulose phthalate. These preparations can contain at least one of the fish brain and any parts thereof as an active ingredient or ingredients, at a percentage of 0.01 wt % or more, preferably 0.01 to 70 wt %.

When the preparations are prepared, menthol, citric acid and salts thereof, and flavoring agents such as fragrances can be added as needed. In addition, the food intake regulator obtained according to the present invention can also be used with other ingredients that are useful for the desired treatment.

The food intake regulator according to the present invention can be administrated orally or parenterally, i. e., subcutaneously, intravenously or intraperitoneally, other than intracerebroventricular administration. The dosage varies depending on the animal species, the race, sex, symptoms, body weight, age, and blood pressure of the patient to be treated, the mode of administration. Therefore, there is no fixed general dosage regimen. When the food intake regulator is orally administered to an adult human, its dosage is usually 0.1 to 2000 mg/kg of body weight/day, preferably 1 to 500 mg/kg of body weight/day and usually administered once a day, or in 2 or 3 times as divided daily doses. However, the dosage can be appropriately selected depending on the degree of the symptoms.

The fish brain and the parts thereof obtained according to the present invention have an excellent food intake regulation effect. Since the fish brain has no specifically offensive smell, taste, or color, it is easily taken orally. For these reasons, at least one of the fish brain and the parts thereof can also be preferably added to products other than pharmaceuticals. For example, these ingredients can be supplied by adding them to solid foods, semi-solid foods, and liquid foods such as jellies, candies, granule confectionery, tablet confectionery, beverages, yogurts, soups, noodles, rice crackers, Japanese-style confectionery, Western-style confectionery, frozen desserts, baked pastry, and seasonings, respectively. In addition, as non-food products other than pharmaceuticals, these ingredients can also be provided in forms such as cosmetics or sanitary goods, and luxury goods. Examples of quasi drugs, one of these non-food products, include hair restorers and tonics, depilatories, hair dyes, decolorizers, permanent wave agents, bath agents, medicated cosmetics and medicated soaps, medicated toothpastes, refrigerants, underarm deodorants, and talcum powders.

The content of at least one of the fish brain and the parts thereof in these non-pharmaceutical products may be selected depending on the intended use and function of the products. It can be selected for example from the range of 0.01 wt % or more, preferably 0.1 to 70 wt %. Regarding cosmetics, various forms of cosmetics such as lotions, creams, powders, and emulsion gels can be prepared by using various solid, semi-solid, or liquid cosmetic bases, and the food intake regulator or the food intake regulator composition in addition to the other active ingredient(s) used to obtain the target cosmetic effect.

The fish brain and the parts thereof according to the present invention can be added in any step for production of the food intake regulators, pharmaceuticals and quasi drugs.

EXAMPLES

Next, the embodiments for carrying out the present invention are described in detail below by using Examples, but the invention is not limited to the Examples below.

Example 1

(Preparation of Brain substances from Chum Salmon, *Oncorhynchus Keta*)

Brains were extracted from the heads of Chum salmon fishes by treating them carefully so that the brains were not damaged. The brains were rapidly frozen in liquid nitrogen and dried by lyophilization. The lyophilized brain product from the Chum salmon fishes were obtained in an amount of 12 mg per one fish.
(Test Example)

Male SD rats (Sprague-Dawley, body weight of 275±25 g) were housed and fed in 45×23×15-cm APECR cages, five rats per cage. The rats were acclimated for 1 week or more on a 12-h light/12-h dark cycle at a room temperature of 22 to 24° C. and a humidity of 60 to 80% with free access to food and water before the test. The rats used for the test were fasted for 12 hours overnight before initiation of the test. After fasting, a sample obtained by homogenizing the lyophilized brain product in a 0.5% carboxymethyl cellulose solution was administrated to each of the rats in the treatment group though a stomach tube in the ratio of 500 mg/kg/5 mL and, then, their food intakes were measured 1, 2, 4, and 6 after administration.

In contrast, in the control group, saline was orally administered by force in the same matter as above and their food intakes were measured in the same way.
(Test Results)

As shown in FIG. 1, it was confirmed that the fish brain according to the present invention acts to significantly inhibit or suppress food intake.
(Preparation of Formulation)
(1) Food Intake Suppression (Tablets)
  Salmon brain lyophilized product: 100 mg
  Lactic acid: 670 mg
  Potato starch: 150 mg
  Crystalline cellulose: 60 mg
  Light silicic anhydride: 50 mg The above components were mixed. A solution prepared by dissolving 30 mg of hydroxypropyl cellulose in ethanol (10 weigh % of hydroxypropyl cellulose) was added to the mixture of the above components and kneaded to obtain particles. The particles were extruded through a screen having the pore size of 0.8 mm to obtain granules. After drying the granules, 15 mg of magnesium stearate was added and tablets were obtained by stamping one tablet per 200 mg.
(2) Food Intake Regulation Agent for Treatment (Injection)
  Salmon brain lyophilized product: 30 mg The above component was dispersed in 2 mL of a 5% mannitol aqueous solution and filled in ampules. The ampules were then sealed under the sterile condition.

As mentioned above, the effect of the food intake regulator was noted by allowing the rats to take the fish brain. This shows that the fish brain is useful in improving and treating as well as preventing obesity, and that they can be used as pharmaceuticals, quasi drugs, health foods, functional foods, and other products having the above bioactivity

What is claimed is:

1. A method of suppressing food intake in a mammalian subject, comprising
    orally administering an active ingredient to a mammalian subject in an effective amount to suppress food intake, wherein the active ingredient is at least one of a lyophilized fish brain, lyophilized parts thereof and a lyophilized fish pituitary gland.

2. A method according to claim 1, wherein the active ingredient is administered in an amount selected from a range of 0.1 to 2000 mg/kg body weight/day.

3. A method according to claim 1, wherein the active ingredient is administered in a form of a composition comprising the active ingredient and a carrier or a diluent.

4. A method according to claim 1, wherein the active ingredient is formulated in a form of a pharmaceutical, a food or a quasi drug.

5. An oral food intake suppressing composition for a administration to a mammalian subject comprising
    an amount of an active ingredient effective and to suppress food intake
    a carrier or a diluent,
    wherein the active ingredient is at least one of a lyophilized fish brain, lyophilized parts thereof and a lyophilized fish pituitary gland.

6. The oral composition according to claim 5, wherein the active ingredient is present in an amount of 0.1 weight % to 70 weight % of the oral composition.

7. A composition according to claim 5, which is a pharmaceutical, a quasi drug or a food.

8. The method of claim 1, wherein the lyophilized lyophilized fish brain is obtained by
    extracting a fish brain from a fish;
    freezing the extracted fish brain; and
    drying the frozen fish brain under a reduced pressure to obtain the lyophilized fish brain.

9. The oral composition of claim 5, wherein the lyophilized lyophilized fish brain is obtained by
    extracting a fish brain from a fish;
    freezing the extracted fish brain; and
    drying the frozen fish brain under a reduced pressure to obtain the lyophilized fish brain.

* * * * *